(12) United States Patent
Bulinski et al.

(10) Patent No.: US 7,759,512 B2
(45) Date of Patent: Jul. 20, 2010

(54) AQUEOUS METHODS FOR MAKING FLUORINATED SULFONATE ESTERS

(75) Inventors: Michael J. Bulinski, Houlton, WI (US); William M. Lamanna, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/176,600

(22) Filed: Jul. 21, 2008

(65) Prior Publication Data

US 2010/0016624 A1 Jan. 21, 2010

(51) Int. Cl.
C07C 309/04 (2006.01)
(52) U.S. Cl. .......................................... 558/54; 558/53
(58) Field of Classification Search ........................ None
See application file for complete search history.

(56) References Cited

U.S. PATENT DOCUMENTS

| | | | | |
|---|---|---|---|---|
| 3,919,295 | A | * | 11/1975 | Wechsberg et al. .......... 562/113 |
| 4,927,962 | A | * | 5/1990 | Aramaki et al. ............. 562/113 |
| 6,479,698 | B1 | * | 11/2002 | Pevere et al. ................ 562/113 |
| 6,599,922 | B2 | * | 7/2003 | Vigano et al. ............... 514/331 |
| 2009/0143613 | A1 | * | 6/2009 | Uotani et al. ............... 562/113 |

FOREIGN PATENT DOCUMENTS

| | | | |
|---|---|---|---|
| GB | 1143481 | * | 2/1969 |
| GB | 2065112 | * | 6/1981 |
| WO | WO 2006/064218 A1 | | 6/2006 |

OTHER PUBLICATIONS

DeSimone et al., "Practical Approaches to Green Solvents", Science, 297(5582), 799-803, 2002.*
Hanack et al., "Facile Synthesis of Trifluoro- and Hexafluoroisopropyl Halides", J. Org. Chem., 54, (1989) pp. 1432-1435.
Briza et al., "Electrophilic polyfluoroalkylating agents based on sulfonate esters", Journal of Fluorine Chemistry, 129, (2008) pp. 235-247.
Gandel'sman et al., 1,1-Dihydropolyfluoroalkylation of N-Alkylanilines, J. Org. Chem. USSR, 14, (1978) pp. 808-809.
Raghavanpillai, et al., An efficient stereoselective preparation of cis-perfluoroalkenylzinc reagents [(E)-$R_F$CF=CFZnCl] by the metallation of 1H, 1H-perfluoroalkanes, and their derivatizatin to cis-1-arylperfluuroalkenes [(Z)-$R_F$CF=CFAr], Journal of Fluorine Chemistry, May 2006, vol. 127, pp. 456-470.

* cited by examiner

Primary Examiner—Fiona T Powers
(74) Attorney, Agent, or Firm—Bradford B. Wright

(57) ABSTRACT

Methods of making a fluorinated sulfonate ester include combining a perfluoroalkanesulfonyl halide and a fluorinated alcohol in water in the presence of hydroxide ion, and recovering at least a portion of the resultant fluorinated sulfonate ester.

16 Claims, No Drawings

AQUEOUS METHODS FOR MAKING FLUORINATED SULFONATE ESTERS

TECHNICAL FIELD

The present disclosure relates broadly to methods of making fluorinated sulfonate esters.

BACKGROUND

In the field of fluorochemistry, fluorinated sulfonyl esters are widely used, because of their relatively high reactivity, to introduce fluorinated organic groups into various compounds. More particularly, sulfonate esters (i.e., compounds having the grouping of atoms C—S(=O)$_2$—O—C) are widely used as alkylating agents. This is due in large part to the high reactivity to heterolytic cleavage of the O—C bond; e.g., in the presence of nucleophiles.

SUMMARY

In one aspect, a method of making a fluorinated sulfonate ester comprises mixing in water:
a) a perfluoroalkanesulfonyl halide, wherein the halide comprises fluoride or chloride;
b) a fluorinated alcohol represented by the formula:

$$R_f\text{—}CX_2OH$$

wherein $R_f$ represents a highly fluorinated alkyl group, and each X is independently H, alkyl, aryl, or $R_f$; and
c) a base comprising hydroxide ion and a non-interfering cation; and
d) recovering at least a portion of the fluorinated sulfonate ester.

In some embodiments, the perfluoroalkanesulfonyl halide, the fluorinated alcohol, and the base are added to the water simultaneously.

In another aspect, the present disclosure provides a method of making a fluorinated sulfonate ester, the method comprising:
a) mixing a perfluoroalkanesulfonyl halide and a fluorinated alcohol in water to provide a reaction mixture, wherein the halide comprises fluoride or chloride, wherein the fluorinated alcohol is represented by the formula:

$$R_f\text{—}CX_2OH$$

wherein $R_f$ represents a highly fluorinated alkyl group, and each X is independently H, alkyl, aryl, or $R_f$;
b) adding base to the reaction mixture, wherein the base comprises hydroxide ion and a non-interfering cation; and
c) recovering at least a portion of the fluorinated sulfonate ester.

In some embodiments, the base is selected from the group consisting of alkali metal hydroxides, alkaline earth hydroxides, and combinations thereof.

In yet another aspect, the present disclosure provides a method of making a fluorinated sulfonate ester, the method comprising:
a) mixing an aqueous base and a fluorinated alcohol to provide a reaction mixture, wherein the base comprises hydroxide ion and a non-interfering cation, and wherein the fluorinated alcohol is represented by the formula:

$$R_f\text{—}CX_2OH$$

wherein $R_f$ represents a highly fluorinated alkyl group, and each X is independently H, alkyl, aryl, or $R_f$;

b) adding perfluoroalkanesulfonyl halide to the reaction mixture, wherein the halide comprises fluoride or chloride; and
c) recovering at least a portion of the fluorinated sulfonate ester.

In some embodiments, the aqueous base comprises water and a compound selected from the group consisting of alkali metal hydroxides, alkaline earth hydroxides, and combinations thereof.

In some embodiments, the perfluoroalkanesulfonyl halide comprises a perfluoroalkanesulfonyl fluoride. In some of those embodiments, the perfluoroalkanesulfonyl fluoride comprises 1,1,2,2,3,3,4,4,4-nonafluorobutane-1-sulfonyl fluoride.

In some embodiments, $R_f$ represents a perfluoroalkyl group. In some embodiments, at least one X is H. In some embodiments, $R_f$ represents $CF_3CFHCF_2$—, $H$—$CF_2CF_2$—, or $HCF_2CF_2CF_2CF_2$—.

Methods according to the present disclosure are typically effective for producing fluorinated sulfonate esters in high yield at moderate temperatures (i.e., near ambient temperature) without the need to use organic solvents or organic bases or anhydrous reaction conditions. While sulfonate esters are known in the art as being highly reactive, it is unexpectedly discovered that the aqueous and basic reaction conditions used in the present disclosure do not cause significant hydrolysis of these products under the moderate reaction conditions that are typically used in the practice of the present disclosure. Equally unexpected, is the finding that the perfluoroalkanesulfonyl halides do not extensively hydrolyze under these reaction conditions, but instead react preferentially with the fluorinated alcohol to give high yields of the corresponding sulfonate esters.

As used herein,

"aqueous" means comprising more than an adventitious amount of water (e.g., water-based); and "highly fluorinated" means that the atomic ratio of F atoms to all monovalent atoms combined in a compound or group is at least 0.4; and "non-interfering cation" means a cation that does not react significantly with other components of the reaction mixture.

DETAILED DESCRIPTION

Methods according to the present disclosure are practiced in the presence of water, a significant improvement over the art. For example, neither organic solvents nor anhydrous reaction conditions need to be used. By avoiding organic solvents there is no need to recover or dispose of organic solvents, and there is typically reduced fire hazard and/or toxicity.

While typically no organic solvents are used in the practice of the instant disclosure, if desired, minor amounts of non-interfering, water-miscible organic solvents (e.g., acetone) may be included with the water. Also, varying amounts of non-miscible organic solvents (e.g., $CH_2Cl_2$) may optionally be used as extractants to aid in controlling the reaction or isolating the sulfonate ester product.

Water used in practice of the present disclosure may be pure, or it may contain impurities (e.g., dissolved salts, VOCs, chlorine).

The perfluoroalkanesulfonyl halide may be a perfluoroalkanesulfonyl fluoride, a perfluoroalkanesulfonyl chloride, or a combination thereof, although perfluoroalkanesulfonyl fluorides are most typically used. The perfluoroalkanesulfonyl halide typically contains 1-8 carbon atoms, more typically 2-6 carbon atoms, and even more typically 2-4 carbon atoms, although it may contain more than 8 carbon atoms. Examples of perfluoralkylsulfonyl halides include: perfluormethanesulfonyl fluoride, perfluoroethanesulfonyl fluoride, perfluoro-n-propanesulfonyl fluoride, perfluoroisopropanesulfonyl chloride, perfluoro-n-butanesulfonyl fluoride (i.e., 1,1,2,2,3,3,4,4,4-nonafluorobutane-1-sulfonyl fluoride), perfluoro-n-butanesulfonyl chloride, perfluoroisobutanesulfonyl fluoride, perfluoro-n-pentanesulfonyl fluoride, perfluoro-n-pentanesulfonyl chloride, and perfluorohexanesulfonyl fluoride.

The fluorinated alcohol is represented by the formula:

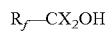

$R_f$—$CX_2OH$ wherein $R_f$ represents a highly fluorinated alkyl group, typically a highly fluorinated alkyl group having from 1 to 6 carbon atoms, and each X is independently H, alkyl, aryl, or $R_f$. When X is an alkyl or aryl group, these groups may optionally be substituted (e.g., with hydrocarbyl groups or halogen or other heteroatom-containing groups). Typically, at least one of X is H, although this is not required. More typically, both X groups are H.

Exemplary fluorinated alcohols include: 2,2,2,-trifluoroethanol; 2,2,3,3-tetrafluoropropan-1-ol; 2,2,3,4,4,4-hexafluorobutanol; and 1,1,1,3,3,3-hexafluoro-2-propanol; 2,2,3,3,4,4,5,5-octafluoropentanol. The fluorinated alcohol may comprise non-interfering heteroatoms (e.g., catenary oxygen atoms).

The base comprises hydroxide ion and a non-interfering counterion; for example, an alkali metal hydroxide, an alkaline earth hydroxide, or a tetraalkylammonium hydroxide. Mixtures of bases may be used. Exemplary bases include sodium hydroxide, potassium hydroxide, lithium hydroxide, calcium hydroxide, magnesium hydroxide, tetrabutylammonium hydroxide, and combinations thereof. The base may also be any base that forms hydroxide ion upon contact with water (e.g., magnesium oxide, potassium carbonate). The base is typically dissolved in water during the esterification reaction (i.e., condensation of the perfluoroalkanesulfonyl halide and the highly fluorinated alcohol to form an ester).

The esterification (i.e., the condensation of the perfluoroalkanesulfonyl halide and the fluorinated alcohol) is typically carried out with stirring (which may be moderate or even vigorous, if desired), typically at a temperature near (above or below) room temperature. For example, temperatures in the range of 20° C. to 40° C. are typically useful. Progress of the reaction can be monitored by any suitable analytical technique. For example, the reaction progress may be monitored by removal of an aliquot and analysis by gas chromatography.

Advantageously, workup of the reaction mixture is typically simple. First, the mixture is filtered to remove any solid material (e.g., salt byproduct(s) or side-product(s)) that precipitates during the reaction. The reaction mixture typically separates into two liquid phases. The lower phase contains the fluorinated sulfonate ester and can be easily separated (e.g., using a separatory funnel). Unreacted starting materials can often be removed by simple vacuum evaporation or distillation techniques.

Objects and advantages of this disclosure are further illustrated by the following non-limiting examples, but the particular materials and amounts thereof recited in these examples, as well as other conditions and, details, should not be construed to unduly limit this disclosure.

EXAMPLES

Unless otherwise noted, all parts, percentages, ratios, etc. in the Examples and the rest of the specification are by weight.

Preparation of 2,2,3,3-tetrafluoropropyl-1,1,2,2,3,3,4,4,4-nonafluorobutane-1-sulfonate 2,2,3,3-tetrafluoropropan-1-ol (202 grams, 1.52 moles, Sinochem Corp., Beijing, China), 1,1,2,2,3,3,4,4,4-nonafluorobutane-1-sulfonyl fluoride (3M Company, Saint Paul, Minn., 465 grams, 1.52 moles) and water (500 g) were combined in a 3-liter, 3-necked round bottom flask. The flask was equipped with a magnetic stirrer, cold water condenser, thermocouple and an addition funnel. Aqueous potassium hydroxide (45 percent by weight, 211.5 g, 1.7 moles, Aldrich Chemical Co., Milwaukee, Wis.) was added dropwise via the addition funnel at such a rate that the temperature did not exceed 35° C. Once the addition of the potassium hydroxide was complete, the mixture was stirred for 16 hours at room temperature. Precipitated salts were then filtered from the mixture and the lower liquid fluorochemical product phase was separated from the upper aqueous phase. Unreacted 2,2,3,3-tetrafluoropropan-1-ol and 1,1,2,2,3,3,4,4,4-nonafluorobutane-1-sulfonyl fluoride were removed from the liquid fluorochemical product phase by atmospheric distillation. Approximately 500 g of 2,2,3,3-tetrafluoropropyl-1,1,2,2,3,3,4,4,4-nonafluorobutane-1-sulfonate was recovered at a purity of 98.9 percent as determined by gas chromatography analysis.

Preparation of 2,2,2-trifluoroethyl-1,1,2,2,3,3,4,4,4-nonafluorobutane-1-sulfonate Potassium hydroxide, 85 percent (145.17 grams, 2.199 moles, Alfa Aesar, Ward Hill, Mass.) and deionized water (300 grams) were charged to a 1-liter, 3-necked, round bottomed flask equipped with an ice bath, mechanical stirrer, condenser, addition funnel, and a thermocouple probe and stirred to dissolve. Once the temperature of the solution had cooled to less than 20° C., 2,2,2-trifluoroethanol, 99+ percent (200.00 grams, 1.999 moles, Aldrich Chemical Co.) was added rapidly with stirring. Perfluorobutanesulfonyl fluoride (664.29 grams, 2.199 moles, 3M Company,) was then added dropwise with stirring while controlling the reaction temperature between 15 and 30° C. using the ice bath to compensate for a mild reaction exotherm. After a total reaction time of 20 hours, stirring was stopped causing separation of two immiscible liquid phases and some insoluble solid precipitate. Gas chromatographic analysis of the lower phase showed that it consisted of 90 percent 2,2,2-trifluoroethyl-1,1,2,2,3,3,4,4,4-nonafluorobutane-1-sulfonate, 9 percent unreacted perfluorobutanesulfonyl fluoride, and 1 percent unreacted 2,2,2-trifluoroethanol. The reaction mixture was filtered by suction through a sintered glass frit to remove solids and the solid filter cake was washed with 300 milliliters of water. The combined filtrate was transferred to a separatory funnel and the lower fluorochemical liquid phase was collected and washed with two 400 milliliter portions of water. The isolated fluorochemical liquid phase was then dried over 3 Angstrom (0.3 nanometer) molecular sieves for three days and then filtered by suction through a 0.45 micron Teflon membrane. Excess perfluorobutanesulfonyl fluoride was removed from the filtrate by vacuum evaporation at 35 to 46° C., 25 mm Hg on a rotary evaporator equipped with a dry ice condenser for about 2.5 hours giving 583.77 grams of clear colorless liquid product. Gas chromatographic analysis indicated that the isolated product was 98.4 percent 2,2,2-trifluoroethyl-1,1,2,2,3, 3,4,4,4-nonafluorobutane-1-sulfonate, with the major impurity being 1.4 percent of residual perfluorobutanesulfonyl fluoride.

Preparation of 2,2,3,4,4,4-hexafluorobutyl 1,1,2,2,3,3,4,4,4-nonafluorobutane-1-sulfonate 2,2,3,4,4,4-hexafluorobutan-1-ol (202 grams, 1.1 moles, Sinochem Corp.), 1,1,2,2,3,3,4,4,4-nonafluorobutane-1-sulfonyl fluoride (332 grams, 1.1 moles, 3M Company) and water (300 g) were combined in a 3-liter, 3-necked round bottom flask. The flask was equipped with a magnetic stirrer, cold water condenser, thermocouple, and addition funnel. Aqueous potassium hydroxide, 45 percent (149.3 grams, 1.22 moles, Aldrich Chemical Co.) was added dropwise via an addition funnel at such a rate that the temperature did not exceed 35° C. Once the addition of the base was complete the mixture was stirred for 16 hours at room temperature. Precipitated salts were then filtered from the mixture and the lower liquid fluorochemical product phase was separated from the upper aqueous phase. Unreacted 2,2,3,4,4,4-hexafluorobutan-1-ol and 1,1,2,2,3,3,4,4,4-nonafluorobutane-1-sulfonyl fluoride were removed by atmospheric distillation. Approximately 400 grams of 2,2,3,4,4,4-hexafluorobutyl 1,1,2,2,3,3,4,4,4-nonafluorobutane-1-sulfonate were recovered at a purity of 98.9 percent as measured by gas chromatographic analysis.

Preparation of 1,1,1,3,3,3-hexafluoro-2-propyl-1,1,2,2,3,3,4,4,4-nonafluorobutane-1-sulfonate Potassium hydroxide, 85 percent (21.61 grams, 0.3273 moles, Alfa Aesar) and 60 grams of deionized water were charged to a 500 mL, 3-necked, round bottomed flask equipped with a water bath, mechanical stirrer, condenser, addition funnel, and a thermocouple probe and stirred to dissolve. Once the temperature of the solution had cooled to less than 20° C., 1,1,1,3,3,3-hexafluoro-2-propanol, 99 percent (50.00 grams, 0.2976 moles, Alfa Aesar) was added rapidly with stirring. Perfluorobutanesulfonyl fluoride (98.86 grams, 0.3273 moles, 3M Company,) was then added dropwise with stirring while controlling the reaction temperature between 22 and 25° C. using the water bath to compensate for a mild reaction exotherm. Once addition was complete, a heating mantle and temperature controller were added, and the reaction temperature was held overnight at 25° C. with stirring. After a total reaction time of 23 hours at 25° C. stirring was stopped, causing separation of two immiscible liquid phases and some insoluble solid precipitate.

The reaction mixture was filtered by suction through a sintered glass frit to remove solids and the solid filter cake was washed with 75 mL of water. The combined filtrate was transferred to a separatory funnel and the lower fluorochemical liquid phase was collected and washed with two 100 mL portions of water. The isolated fluorochemical liquid phase (90 grams) was then dried over 3 Angstrom (0.3 nanometer) molecular sieves for 1 week and then filtered by suction through a 0.45 micron Teflon membrane yielding 83.8 grams of filtered product. A small amount of excess perfluorobutanesulfonyl fluoride was removed from the filtrate by vacuum evaporation at 43° C., 25 mm Hg (3.3 Pa) using a rotary evaporator equipped with a dry ice condenser over about 1 hour resulting in 79.3 grams of clear colorless liquid product. Gas chromatographic analysis indicated that the isolated product was 98.8 percent pure 1,1,1,3,3,3-hexafluoro-2-propyl-1,1,2,2,3,3,4,4,4-nonafluorobutane-1-sulfonate.

Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A method of making a fluorinated sulfonate ester, the method comprising mixing in water:
   a) a perfluoroalkanesulfonyl halide, wherein the halide comprises fluoride or chloride;
   b) a fluorinated alcohol represented by the formula:

$R_f$—$CX_2OH$ wherein $R_f$ represents a highly fluorinated alkyl group, and each X is independently H, alkyl, aryl, or $R_f$; and
   c) a base comprising hydroxide ion and a non-interfering cation; and
   d) recovering at least a portion of the fluorinated sulfonate ester.

2. The method of claim 1, wherein the perfluoroalkanesulfonyl halide, the fluorinated alcohol, and the base are added to the water simultaneously.

3. A method of making a fluorinated sulfonate ester, the method comprising:
   a) mixing a perfluoroalkanesulfonyl halide and a fluorinated alcohol in water to provide a reaction mixture, wherein the halide comprises fluoride or chloride, wherein the fluorinated alcohol is represented by the formula:

$R_f$—$CX_2OH$ wherein $R_f$ represents a highly fluorinated alkyl group, and each X is independently H, alkyl, aryl, or $R_f$;
   b) adding base to the reaction mixture, wherein the base comprises hydroxide ion and a non-interfering cation; and
   c) recovering at least a portion of the fluorinated sulfonate ester.

4. The method of claim 3, wherein the perfluoroalkanesulfonyl halide comprises a perfluoroalkanesulfonyl fluoride.

5. The method of claim 4, wherein the perfluoroalkanesulfonyl fluoride comprises 1,1,2,2,3,3,4,4,4-nonafluorobutane-1-sulfonyl fluoride.

6. The method of claim 3, wherein $R_f$ represents $CF_3CFHCF_2$—, H—$CF_2CF_2$—, or $HCF_2CF_2CF_2CF_2$—.

7. The method of claim 3, wherein $R_f$ represents a perfluoroalkyl group.

8. The method of claim 3, wherein at least one X is H.

9. The method of claim 3, wherein the base is selected from the group consisting of alkali metal hydroxides, alkaline earth hydroxides, and combinations thereof.

10. A method of making a fluorinated sulfonate ester, the method comprising:
    a) mixing an aqueous base and a fluorinated alcohol to provide a reaction mixture, wherein the base comprises hydroxide ion and a non-interfering cation, and wherein the fluorinated alcohol is represented by the formula:

$R_f$—$CX_2OH$ wherein $R_f$ represents a highly fluorinated alkyl group, and each X is independently H, alkyl, aryl, or $R_f$;
    b) adding perfluoroalkanesulfonyl halide to the reaction mixture, wherein the halide comprises fluoride or chloride; and
    c) recovering at least a portion of the fluorinated sulfonate ester.

11. The method of claim 10, wherein the perfluoroalkanesulfonyl halide comprises a perfluoroalkanesulfonyl fluoride.

12. The method of claim 11, wherein the perfluoroalkanesulfonyl fluoride comprises 1,1,2,2,3,3,4,4,4-nonafluorobutane-1-sulfonyl fluoride.

13. The method of claim 10, wherein $R_f$ represents $CF_3CFHCF_2-$, $H-CF_2CF_2-$, or $HCF_2CF_2CF_2CF_2-$.

14. The method of claim 10, wherein $R_f$ represents a perfluoroalkyl group.

15. The method of claim 10, wherein at least one X is H.

16. The method of claim 10, wherein the aqueous base comprises water and a compound selected from the group consisting of alkali metal hydroxides, alkaline earth hydroxides, and combinations thereof.

* * * * *